US008678583B2

United States Patent
Cohen

(10) Patent No.: US 8,678,583 B2
(45) Date of Patent: Mar. 25, 2014

(54) TRIFOCAL IOL USING DIFFRACTION

(76) Inventor: Allen Louis Cohen, Manakin Sabot, VA (US)

( * ) Notice: Subject to any disclaimer, the term of this patent is extended or adjusted under 35 U.S.C. 154(b) by 0 days.

(21) Appl. No.: 13/467,206

(22) Filed: May 9, 2012

(65) Prior Publication Data

US 2012/0224138 A1  Sep. 6, 2012

(51) Int. Cl.
 *G02C 7/04* (2006.01)
(52) U.S. Cl.
 USPC ............... 351/159.11; 351/159.1; 351/159.12
(58) Field of Classification Search
 USPC ............... 351/159.05, 159.06, 159.1–159.12, 351/159.14, 159.15; 623/6.28, 6.3, 6.31
 See application file for complete search history.

(56) References Cited

U.S. PATENT DOCUMENTS

| 5,017,000 | A | * | 5/1991 | Cohen .................. 351/159.41 |
| 5,116,111 | A | * | 5/1992 | Simpson et al. ......... 351/159.44 |
| 5,129,718 | A | * | 7/1992 | Futhey et al. ............ 351/159.44 |
| 2005/0264757 | A1 | * | 12/2005 | Morris et al. ................. 351/168 |

* cited by examiner

*Primary Examiner* — Evelyn A Lester
*Assistant Examiner* — William Alexander

(57) ABSTRACT

Mutifocal diffractive lenses are generally designed with concentric annular zones comprising blazed steps of equal area. Trifocal diffractive lenses differ in the intensity of light that they diffract into each of their three different powers. Usually, this light distribution has been adjusted by varying the step heights of the blazed steps within the annular zones. This invention discloses a trifocal diffractive lens wherein the equal area annular zones are further subdivided into two sub-zones wherein each sub-zone comprises a discrete blazed step. The sub-zones of this invention may be of unequal area. This allows the light distribution at its focal powers to be adjusted by varying not only the step heights of the blazed steps of the sub-zones, but also the relative areas of the sub-zones. The present invention allows for an increased flexibility in the design of multifocal diffractive lenses.

20 Claims, 9 Drawing Sheets

TRIFOCAL IOL USING DIFFRACTION

BACKGROUND OF THE INVENTION

1. Field of the Invention

Many people, particularly the aged, develop cataracts necessitating the removal of the natural crystalline lens from within their eye. Intraocular lenses (IOLs) are artificial (prosthetic) lenses that are used as a replacement for the natural lens of the human eye. The present invention relates generally to multifocal diffractive lenses, and more particularly to trifocal diffractive IOLs. Trifocal diffractive IOLs have three distinct powers that provide a patient, who has undergone cataract surgery, with far, intermediate, and near vision prescriptions.

2. Description of the Prior Art

A diffractive lens generally comprises a number of concentric annular zones of equal area with optical steps separating the adjacent annular zones. The width of the zones determines the separation between the diffractive powers (vision prescriptions) of the lens, the separation of the diffractive powers increasing with decreasing zone width.

a. Diffraction Bifocals

Diffractive lenses have been known and analyzed since the 1800s, but it wasn't until the 1960s that they were first used to correct human vision. The earliest such ophthalmic diffractive lens had a Fresnel Phase Plate design with "flat" zones, as disclosed in 1967 by Gunter Überschaar in his German Patent Publication 1,235,028. This Fresnel Phase Plate design used ½ wave deep flat steps which produced a bifocal lens that divided light equally between the +1 and −1 diffraction orders.

We can better understand the Überschaar lens by referring to FIG. 1a where we see a front view of a contact lens showing the boundaries $r_1, r_2, r_3, \ldots$ of the flat annular zones 1 according to his invention. FIG. 1b is a cross-section view showing the flat annular zones 1 comprising the anterior diffractive surface 2 of the contact lens 3 of FIG. 1a. The flat annular zones 1 are shown schematically in FIG. 1c with the vertical axis representing step height S and the horizontal axis representing $r^2$, where r is the radial distance from the center of the contact lens. Since all the annular zones in this diffractive lens have equal area, the zone boundaries $r_1, r_2, r_3, \ldots$ are equally spaced in $r^2$-space.

In the 1980s Cohen (U.S. Pat. Nos. 4,210,391; 4,338,005; 4,340,283; 5,054,905; 5,056,908; 5,117,306; 5,120,120; 5,121,979; 5,121,980; 5,144,483) and Freeman (U.S. Pat. Nos. 4,637,697; 4,642,112; 4,655,565; 4,641,934) disclosed the first ophthalmic diffractive lenses with blazed (angled) zones exhibiting a saw-toothed profile. These blazed designs used ½ wave deep substantially parabolic profiles which created bifocal lenses that divided light equally between the 0th and +1 diffraction orders.

FIG. 2a is a cross-section of the blazed annular zones 4 comprising the anterior diffractive surface 5 of an IOL 6 according to the inventions of Cohen and Freeman. The blazed annular zones 4, of this IOL, are shown schematically in FIG. 2b with the vertical axis representing step height S and the horizontal axis representing $r^2$, where r is the radial distance from the center of the contact lens.

We also see in FIG. 2b that each blazed annular zone 4 comprises a discrete step surface 4a and a blazed surface 4b. In $r^2$-space the blazed surfaces 4b take a linear form, and the zone boundaries $r_1, r_2, r_3, \ldots$ are equally spaced. But, it should be recognized that, when graphed in r-space (as opposed to $r^2$-space), not only will the zones be unequally spaced, but the profile of the blazed surfaces 4b will take on a quadratic form as illustrated in FIG. 2c.

In 2003, Fiala (U.S. Pat. No. 6,536,899) disclosed a bifocal that divided each annular zone into two sub-zones. The sub-zones were designed as a way to eliminate the sharp steps of the standard blazed step bifocals. In his lens design, each annular zone comprised a main sub-zone of larger area and a phase sub-zone of smaller area and narrower width. In particular, he designed his phase sub-zones to cause the necessary phase shift needed to replace the optical steps of a diffractive lens.

The annular zones of the Fiala invention, are shown schematically in FIG. 3 with the vertical axis representing the step height S and the horizontal axis representing $r^2$, where r is the radial distance from the center of the lens. The annular zones of this lens, bounded on the outside by the radii $r_1, r_2, r_3, \ldots$, are each divided into two sub-zones 7a and 7b which are generally of unequal area. While the sub-zones are of unequal area, the ratio of their areas remains unchanged from zone to zone.

b. Diffraction Trifocals

By the early 2000s, commercial diffractive IOLs were widely available as bifocals with blazed zone designs providing a split of light between the 0th and +1 diffraction orders. However, in 1994, Swanson (U.S. Pat. No. 5,344,447) had already disclosed a trifocal diffractive IOL based on a Fresnel Phase Plate design. This design uses ⅓ wave deep flat steps, thereby producing a trifocal lens that divides light equally between the +1, 0th, and −1 diffraction orders. A modification of this trifocal design was disclosed in 1998 by Kosoburd (U.S. Pat. No. 5,760,871).

Then, in 2011, Schwiegerling (U.S. Pat. App. Pub. 2011/0292335) and Gatinel (Intn'l. Pat. App. Pub. WO 2011/092169) proposed designs r a diffractive trifocal with blazed steps. These designs use equal area blazed annular zones with alternating step heights, thereby creating a trifocal lens that divides light between the 0th, +1, and +2 diffraction orders.

The alternating annular zones 8a and 8b of these trifocal designs, are shown schematically in FIG. 4. We can see that all of the zones 8a have the step height Δa, while all of the alternate zones 8b have the step height Δb, where the step height Δb is not equal to the step height Δa.

c. Apodization

Meanwhile, it was seen to be advantageous to find designs that would provide a varying split of light between the different diffraction orders as the pupil of the eye opens and closes. In 1997 Simpson (U.S. Pat. No. 5,699,142) disclosed an "apodized" design wherein the light distribution between the 0th and +1 diffraction orders could be controlled by varying the step height (zone depth) of the individual zones. Since then, within the context of ophthalmic diffractive lenses, apodization has come to mean the gradual reduction of the step heights starting at the center of the lens and moving outward toward the periphery. Apodization has been widely adopted for multifocal diffractive IOLs and allows the light distribution between the 0th and +1 diffraction orders to vary as the pupil of the eye opens and closes. FIG. 5a illustrates the design profile of a typical apodized diffractive bifocal wherein the peaks of the blazed steps 9 follow a line of apodization 10.

In addition to the constant depth reduction across each zone progressing from the central zone outward, Simpson included a phase shift across each zone, again progressing from the central zone outward. This phase shift was introduced to allow the light from the various zones of different depths to all remain in phase. FIG. 5b illustrates the design profile of a typical apodized and phase shifted diffractive bifocal wherein the peaks of the blazed steps 11 follow a line of apodization 12 and the blazed steps are also phase shifted to center on a phase shift line 13.

Schwiegerling and Gatinel also incorporated apodization schemes in their trifocal inventions. FIG. 6a illustrates their trifocal design with apodization of the alternate blazed steps 14a and 14b. FIG. 6b illustrates their trifocal design with both apodization and phase shifting of the alternate blazed steps 15a and 15b. Finally, FIG. 6c illustrates a double apodization scheme for a diffractive trifocal lens as proposed by Schwiegerling wherein the peaks of the alternate blazed steps 16a and 16b each follow the different, non-parallel, lines of apodization 17 and 18 respectively.

BRIEF SUMMARY OF THE INVENTION

Prior art multifocal diffractive lenses, employ multiple concentric annular zones of equal area. This invention relates to those multifocal diffractive lens designs wherein the annular zones comprise blazed steps and more particularly to such lenses that are designed to have three different focal powers. Trifocal lenses of this type differ in the intensity of light that they diffract into each of their three different powers. In general, this light distribution has been adjusted by varying the step heights of the blazed steps within the annular zones.

It is an object of the present invention to provide a multifocal diffractive lens wherein each annular zone is divided into two sub-zones and wherein each sub-zone comprises a discrete blazed step.

It is a further object of the present invention to provide a multifocal lens that allows the light distribution at its focal powers to be adjusted by varying not only the step heights of the blazed steps of the sub-zones, but also the relative areas of the sub-zones. This allows for an increased flexibility in the design of multifocal diffractive lenses.

BRIEF DESCRIPTION OF THE DRAWINGS

FIG. 1b is a cross-section view showing the flat annular zones 1 comprising the anterior diffractive surface 2 of the contact lens 3 of FIG. 1a.

DETAILED DESCRIPTION OF THE INVENTION

A lens, according to the present invention, comprises a number of equal area annular zones wherein at least some of the annular zones are subdivided into two sub-zones of equal or unequal areas each of said sub-zones comprising a discrete blazed step.

Figure 1A:
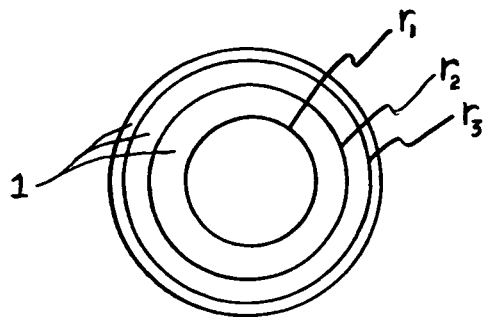
FIG. 1a shows a front view of a contact lens of the Überschaar design, showing the boundaries $r_1, r_2, r_3, \ldots$ of the flat annular zones of the Überschaar invention.
Figure 1B:
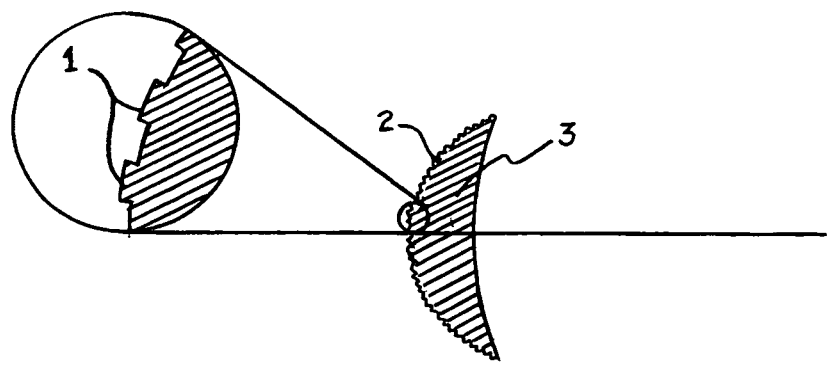
Figure 1C:
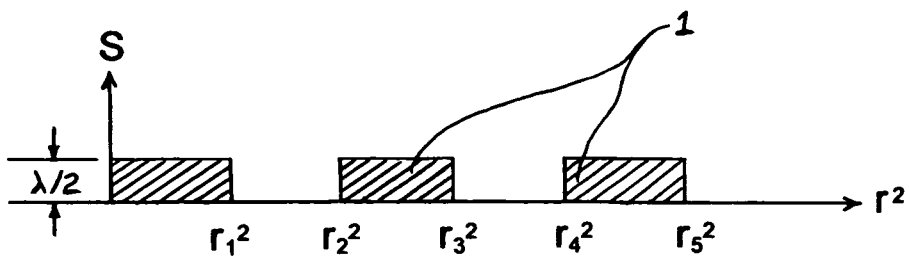
FIG. 1c is a schematic representation of the flat annular zones 1 of the contact lens 3 of FIG. 1b, where the vertical axis represents the step height S, the horizontal axis represents $r^2$, and r is the radial distance from the center of the contact lens.
Figure 2A:
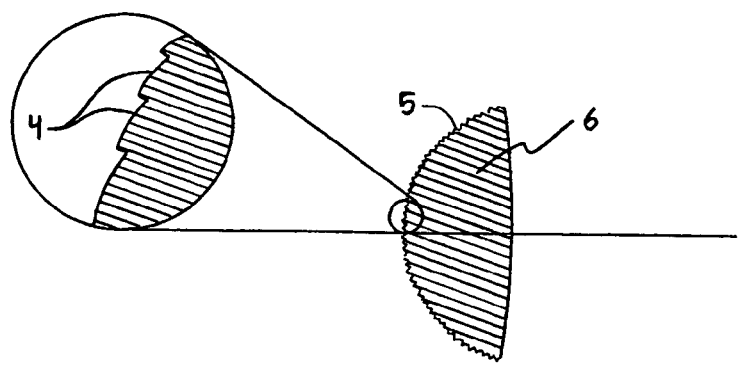
FIG. 2a is a cross-section of the blazed annular zones 4 comprising the anterior diffractive surface 5 of an IOL 6 according to the inventions of Cohen and Freeman.
Figure 2B:
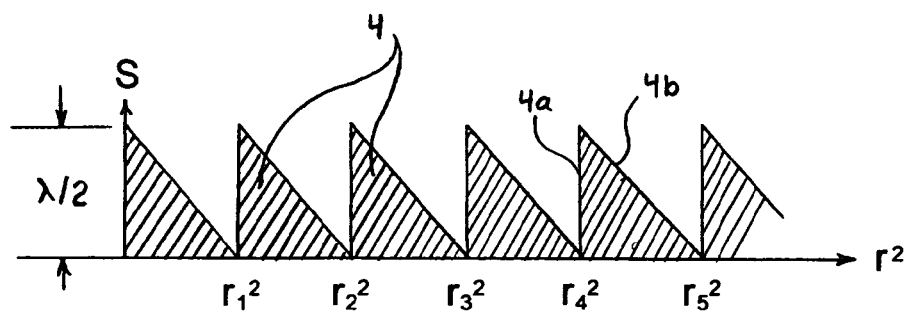
FIG. 2b is a schematic representation of the blazed annular zones 4, of the IOL of FIG. 2a, where the vertical axis represents the step height S, the horizontal axis represents $r^2$, and r is the radial distance from the center of the contact lens.
Figure 2C:
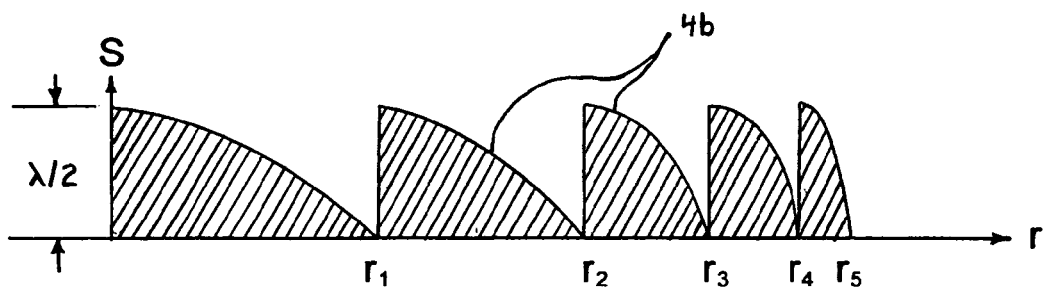
FIG. 2c shows the blazed surfaces 4b, of the blazed zones of the IOL of FIG. 2a, taking on a quadratic form when graphed in r-space as opposed to $r^2$-space.
Figure 3:
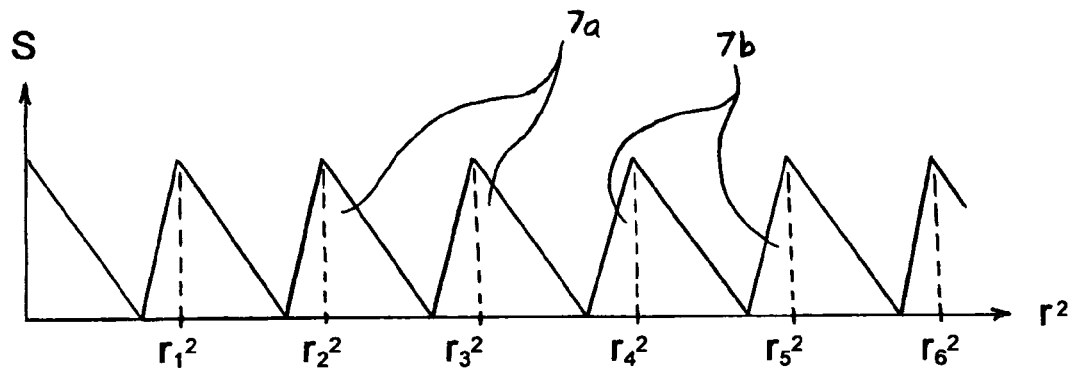
FIG. 3 is a schematic representation of a lens design according to the Fiala invention, showing the sub-zones 7a & 7b, where the vertical axis represents the step height S, the horizontal axis represents $r^2$, and r is the radial distance from the center of the contact lens.
Figure 4:
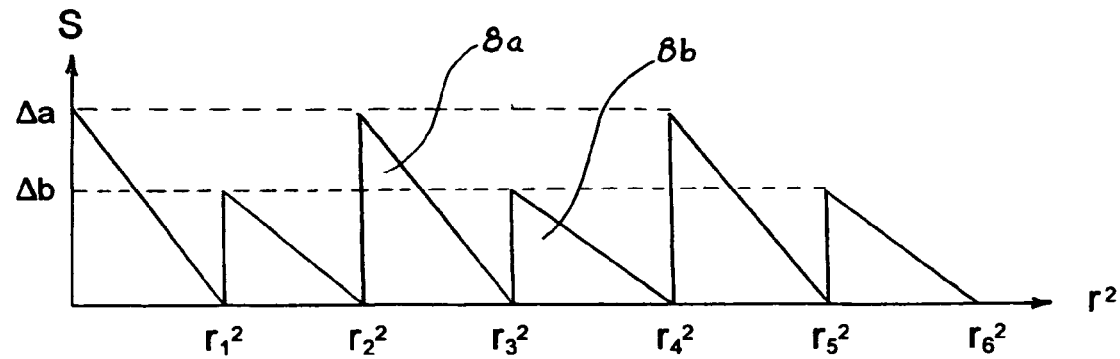
FIG. 4 is a schematic representation illustrating the alternating annular zones 8a and 8b of the trifocal designs of Schwiegerling and Gatinel.
Figure 5A:
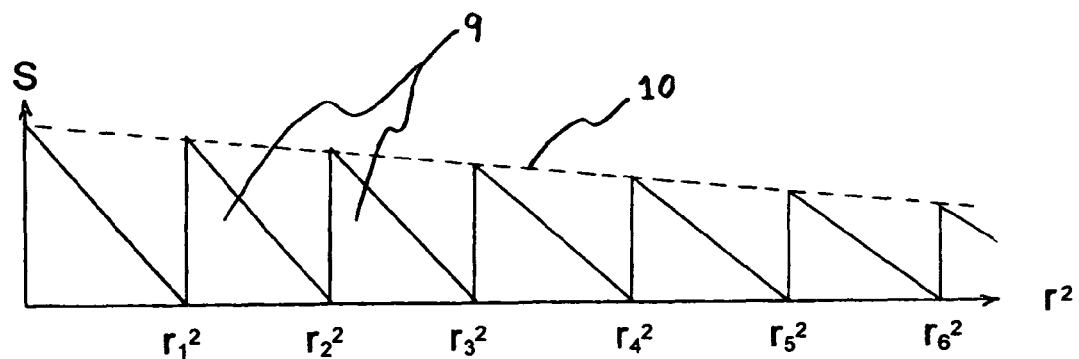
FIG. 5a illustrates the design profile of a typical apodized diffractive bifocal wherein the peaks of the blazed steps 9 follow a line of apodization 10.
Figure 5B:
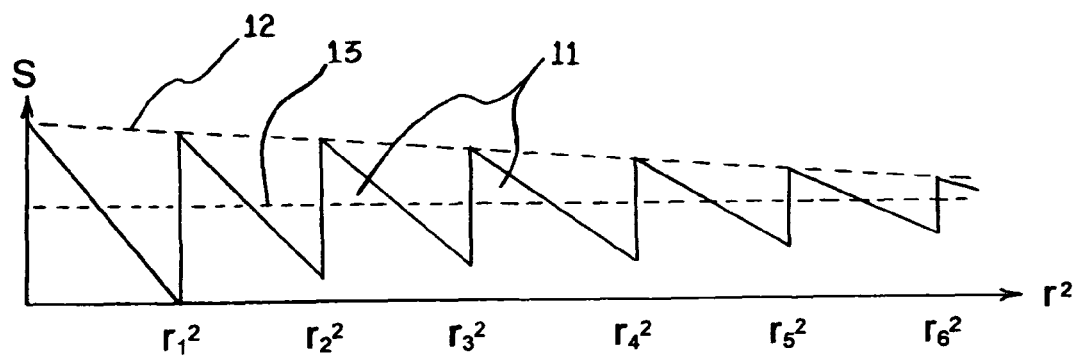
FIG. 5b illustrates the design profile of a typical apodized and phase shifted diffractive bifocal wherein the peaks of the blazed steps 11 follow a line of apodization 12 and the blazed steps are also phase shifted to center on a phase shift line 13.
Figure 6A:
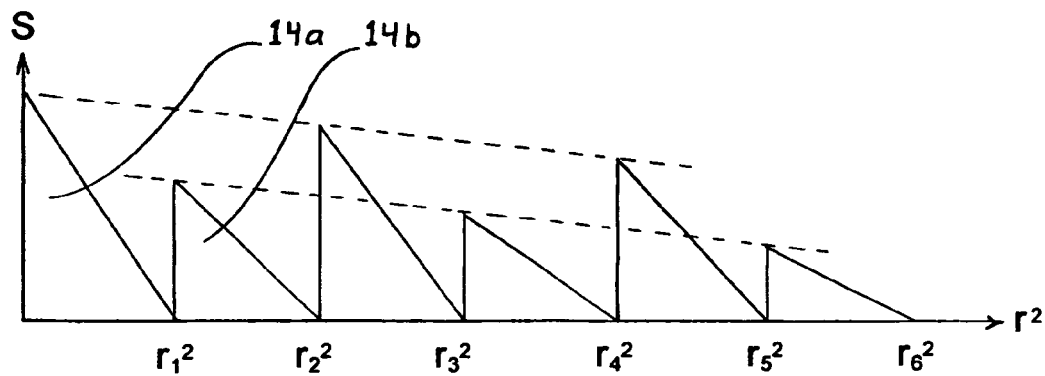
FIG. 6a illustrates the Schwiegerling and Gatinel trifocal design with apodization of the alternate blazed steps 14a and 14b.
Figure 6B:
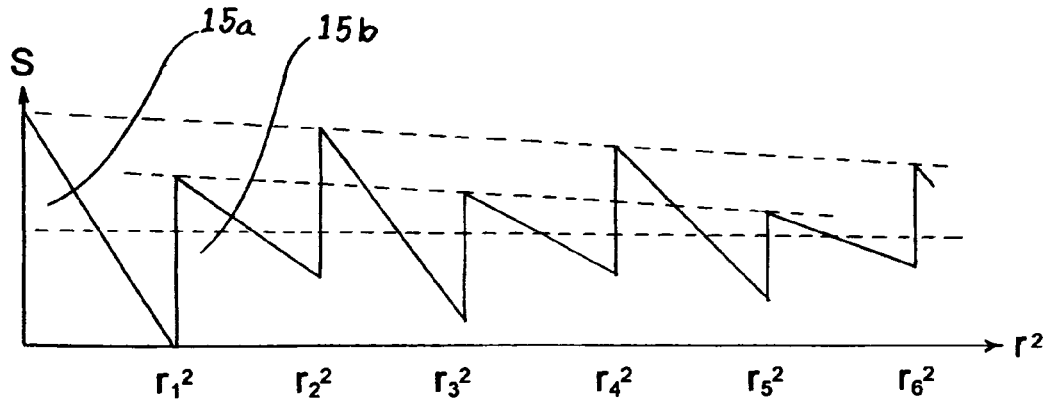
FIG. 6b illustrates the Schwiegerling and Gatinel trifocal design with both apodization and phase shifting of the alternate blazed steps 15a and 15b.
Figure 6C:
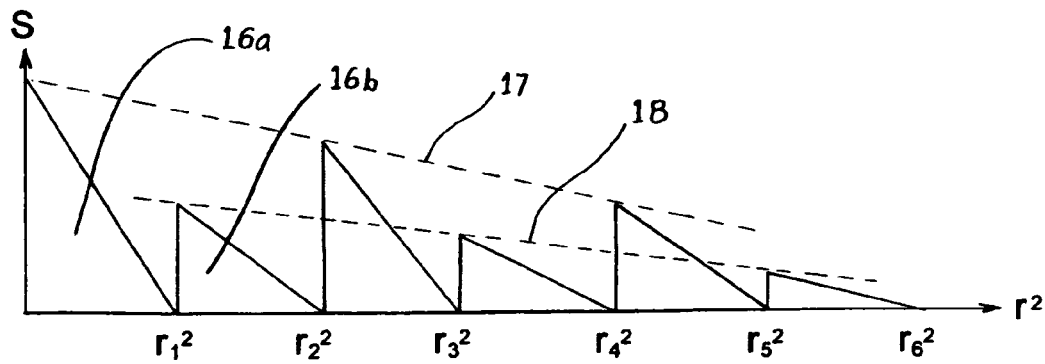
FIG. 6c illustrates a double apodization scheme for a diffractive trifocal lens as proposed by Schwiegerling wherein the peaks of the alternate blazed steps 16a and 16b follow the different nonparallel lines of apodization 17 and 18 respectively.
Figure 7A:
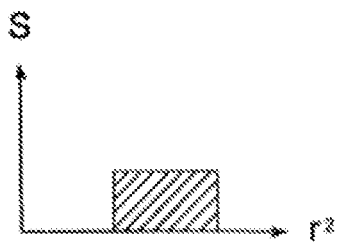
FIG. 7a illustrates a flat step which introduces a constant phase shift to light passing through said step.
Figure 7B:
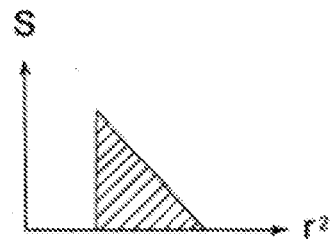
FIG. 7b illustrates a pure blazed step which introduces a varying phase shift to light passing through said step.
Figure 7C:
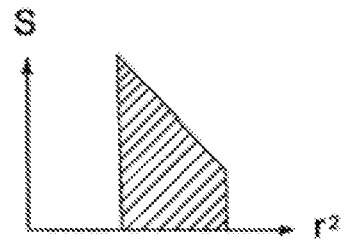
FIG. 7c illustrates a combination step which may be referred to as a blazed step with a phase shift.

For the purposes of this invention, a "discrete blazed step" may take the form of (1) a flat step (herein illustrated in FIG. 7a) which introduces a constant phase shift to light passing through said step, (2) a pure blazed step (herein illustrated in FIG. 7b) which introduces a varying phase shift to light passing through that step, or (3) a combination step (herein illustrated in FIG. 7c) which may be referred to as a blazed step with a phase shift.

By way of example, we consider a lens wherein all of the annular zones are of equal area, all of the annular zones are subdivided into two sub-zones of equal or unequal areas and each sub-zone comprises a discrete blazed step. In this case, the radial distance from the center of the lens to the outer boundary of the 1st annular zone may be given by $r_1$, to the outer boundary of the mth annular zone by $r_m = mr_1^2$, and the area of each annular zone will then be equal to $\pi(r_m^2 - r_{m-1}^2) = \pi r_1^2$.

Figure 8A:
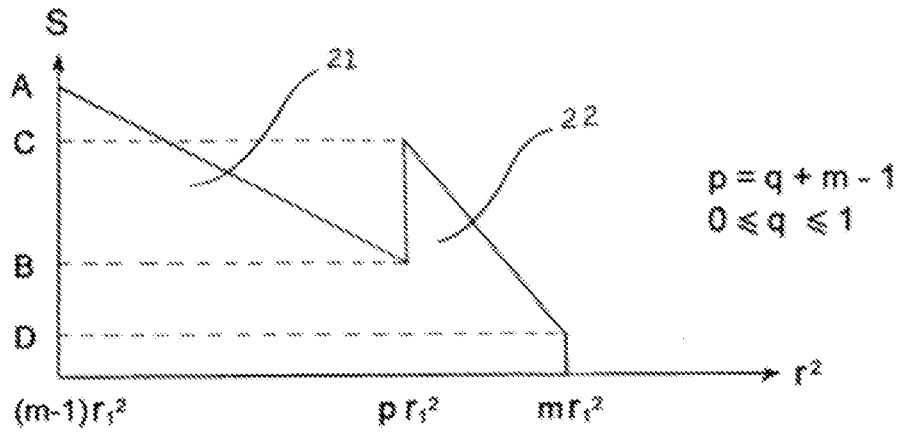
FIG. 8a illustrates the mth zone of a trifocal lens of this invention, wherein the vertical axis represents the step height S of the discrete blazed sub-zones 21 and 22, and the horizontal axis represents $r^2$, where r is the radial distance from the center of the contact lens.

The mth annular zone of this lens is illustrated in FIG. 8a where we see its two sub-zones separated at the boundary $r_q^2 = p\, r_1^2 = (q+m-1)\, r_1^2$ where q is a parameter ranging between 0 and 1. In this case, the area of the 1st sub-zone 21 is equal to $q\,\pi\,r_1^2$ while the area of the 2nd sub-zone 22 is equal to $(1-q)\,\pi\,r_1^2$. In general, q may be different for each annular zone so that q=q(m), but the combined area of the two sub-zones of each annular zone will always equal $\pi r_1^2$ which is the area of the mth annular zone.

Figure 8B:
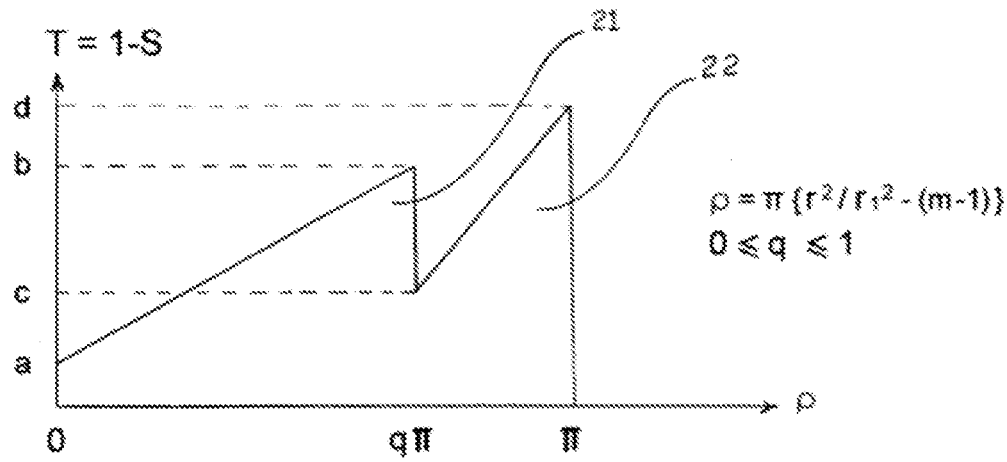
FIG. 8b illustrates the annular zone illustrated in FIG. 8a graphed in T-ρ space where T=1−S is the inverse profile of said annular zone and $\rho = \pi \{r^2/r_1^2 - (m-1)\}$.

For the purposes of analysis we now introduce a change of variables from Step Height S to T=1−S, and from radial distance r to $\rho = \pi\,\{r^2/r_1^2 - (m-1)\}$. Graphing the profile of FIG. 8a using the new variables T and ρ, FIG. 8b shows an illustration of the mth annular zone in T-ρ space. It should be clear that the maximum and minimum heights of sub-zones 21 and 22 given by A, B, C and D as shown in FIG. 8a, are now represented by the new variables a=(1−A), b=(1−B), c=(1−C), and d=(1−D) as shown in FIG. 8b.

A lens of this type will focus incident light into the various diffraction orders α, where α=0, ±1, ±2, . . . and the corresponding optical powers of this lens are $P_\alpha = 2\alpha\lambda/r_1^2$ with λ being the design wavelength. To calculate the intensity of light at each of these diffraction orders, we start by finding the amplitude of light A1 and A2 focussed by the 1st and 2nd sub-zones of zone m as below:

$$A_1 = (1/\pi)\int_0^{q\pi} \exp\{2\pi i[(\alpha/\pi)\rho - (R/\pi)\rho - a]\}\,d\rho \quad (1)$$

$$A_2 = (1/\pi)\int_{q\pi}^{\pi} \exp\{2\pi i[(\alpha/\pi)\rho - (R'/\pi)\rho - (d-R')]\}\,d\rho \quad (2)$$

where α=diffraction order, $$R = (b-a)/q, \quad (4)$$

$$R' = (d-c)/(1-q) \quad (5)$$

Carrying out the integration gives us:

$$A1 = q\exp[i\pi Y]\,\mathrm{sinc}\{q(\alpha-R)\} \quad (6)$$

$$A2 = (1-q)\exp[i\pi Z]\,\mathrm{sinc}\{(1-q)(\alpha-R')\} \quad (7)$$

where $Y = q(\alpha-R) - 2a$ (8)

and $Z = (1+q)(\alpha-R') - 2(d-R')$ (9)

are the phase angles of A1 and A2 respectively
Finally, we define Am (α), Im (α), and ωm (α) as follows:

$Am(\alpha)$=the amplitude of light focussed by zone m at diffraction order α

$Im(\alpha)$=the Intensity of light focussed by zone m at diffraction order α

$\omega m(\alpha)$=final phase angle of the light due to the first m zones

We can calculate the intensity, and phase angle of the light focussed by zone m at each diffraction order α as:

$$Im(\alpha) = Am^2(\alpha) = A1^2 + A2^2 + 2\,A1\,A2\,\cos\{\pi(Y-Z)\} \quad (10)$$

and the phase angle ωm (α) of the light focussed by zone m at diffraction order α as $$\omega m(\alpha) = \tan^{-1}\{(A1\sin Y + A2\sin Z)/(A1\cos Y + A2\cos Z)\} \quad (11)$$

Figure 9:
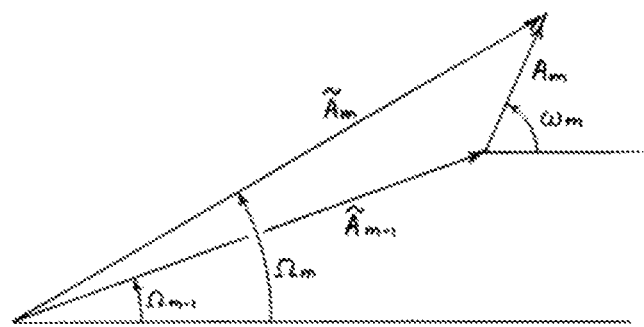
FIG. 9 illustrates zone by zone vector addition of the light amplitude diffracted into the various orders of diffraction.

But the total intensity of light at any diffractive order must be calculated by vector addition of the individual contributions to the light amplitude of each zone m. We start by defining $\tilde{A}m(\alpha)$≡total amplitude of light due to the first m zones $\hat{I}m(\alpha)$≡total intensity due to the first m zones $\Omega m(\alpha)$≡final phase angle of the light due to the first m zones Finally, zone by zone vector addition (geometrically illustrated in FIG. 9) leads to the following recursive formulas:

$$\hat{I}m(\alpha) = \tilde{A}m^2 = [(m-1)/m]^2 \hat{I}m-1 + (1/m)^2\,Im^2 + 2\,[(m-1)/m^2]\hat{I}m-1\,Im\,\cos(\omega m-1 - \Omega m) \quad (12)$$

$$\Omega_m(\alpha) \equiv \tan^{-1}\left\{\frac{I_{m-1}\sin\Omega_{m-1}\{(m-1)/m\} + (1/m)I_m\sin\omega_m\{1/m\}}{I_{m-1}\cos\Omega_{m-1}\{(m-1)/m\} + (1/m)I_m\cos\omega_m\{1/m\}}\right\} \quad (13)$$

Figure 10:
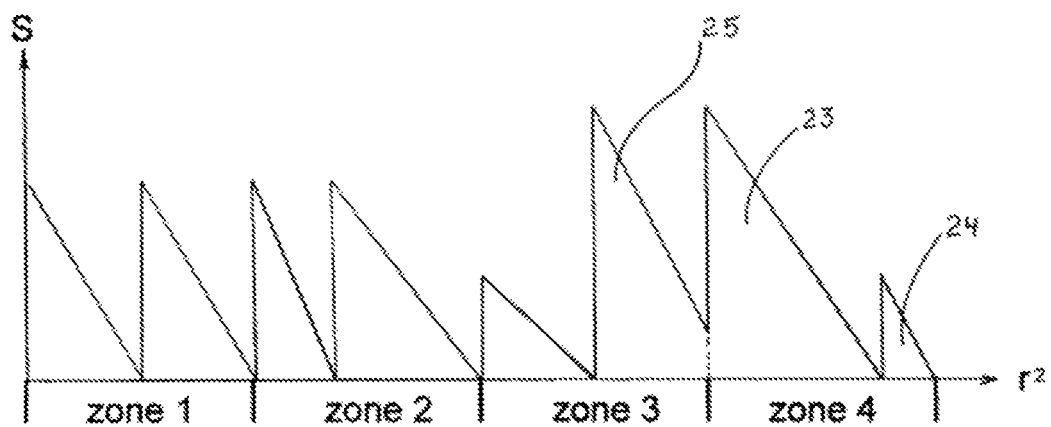
FIG. 10 illustrates a general 4 zone lens according to this invention.

FIG. 10, which is appropriate for a front page view in this application, is illustrative of the present invention. In particular, FIG. 10 illustrates a 4 zone diffraction lens that not only uses different step heights for some of the sub-zones (e.g. sub-zones 23 and 24 of zone 4), but also make use of "micromodulation" wherein the areas of the different sub-zones differ from one annular zone to the next (e.g. between zone 1 and zone 2). In addition, we also see a phase shift incorporated into sub-zone 25 of zone 3.

Figure 11A:
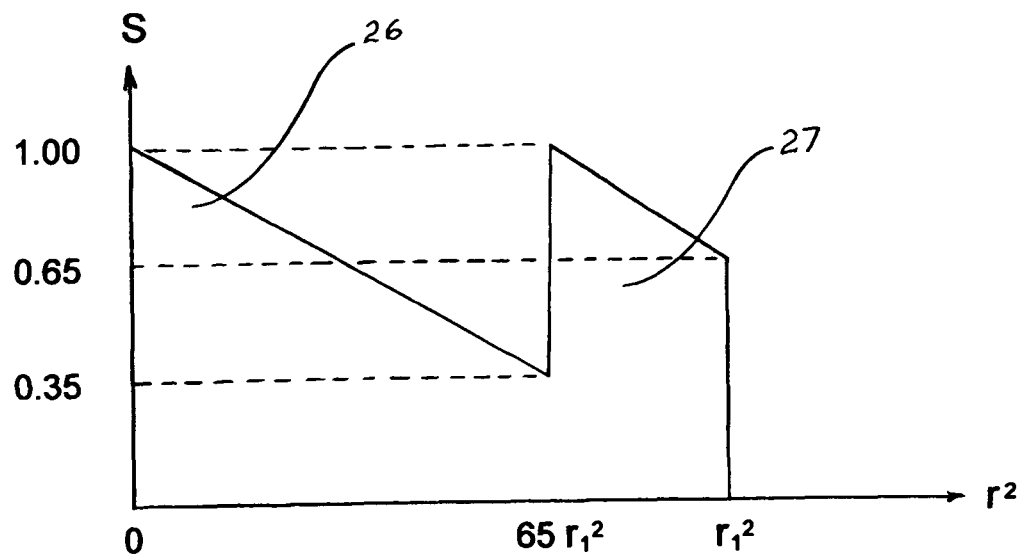
FIG. 11a illustrates a zone profile that produces a trifocal distribution of light.
Figure 11B:
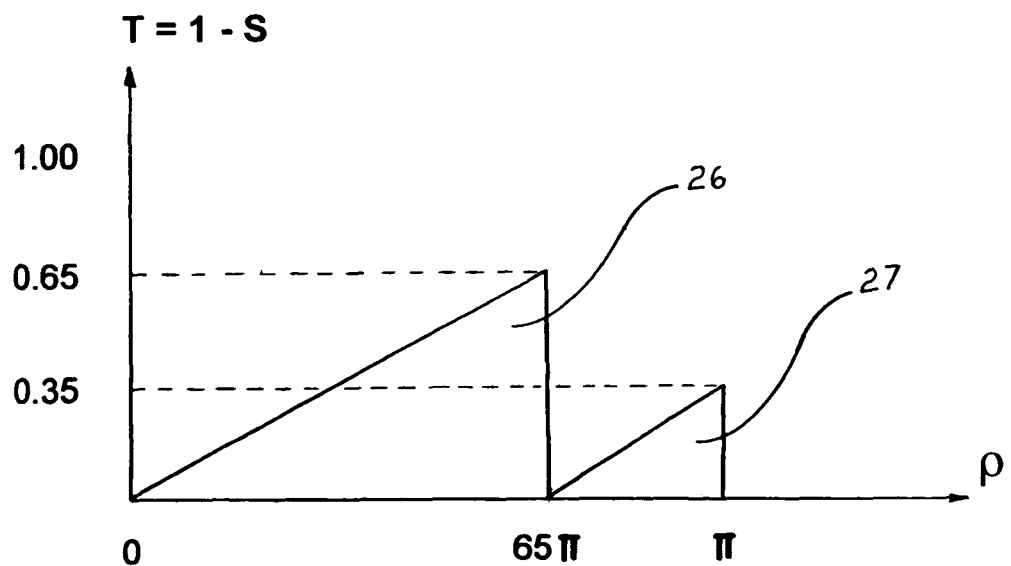
FIG. 11b illustrates the same zone profile of FIG. 10a graphed in T-ρ space.

As a more specific example, let us consider a single zone (shown in FIG. 11a) where the zone profile has the parameters A=1.00, B=0.349, C=1.00, D=0.651, and q=0.652, so that the area of the first sub-zone 26 is 65% of the total zone area while the second sub-zone 27 is 35% of the total zone area. While FIG. 11a shows a graph of this single zone lens profile in S-$r^2$ space, the same lens profile is shown in FIG. 11b in T-ρ space. Now, making use of equation (10) and replacing A, B, C, and D with a=(1−A), b=(1−B), c=(1−C), and d=(1−D), we find that this zone will act as a trifocal by directing about 25% of the incident light into the 0th order, 28% of the incident light into the 1st order, and 25% of the incident light into the 2nd order. These results are shown in Table 1.

TABLE 1

| zone (m) | a | b | c | d | q | Im(0) | Im(1) | Im(2) |
|---|---|---|---|---|---|---|---|---|
| 1 | 0.0000 | 0.6510 | 0.0000 | 0.3490 | .652 | 25% | 28% | 25% |

Figure 12:
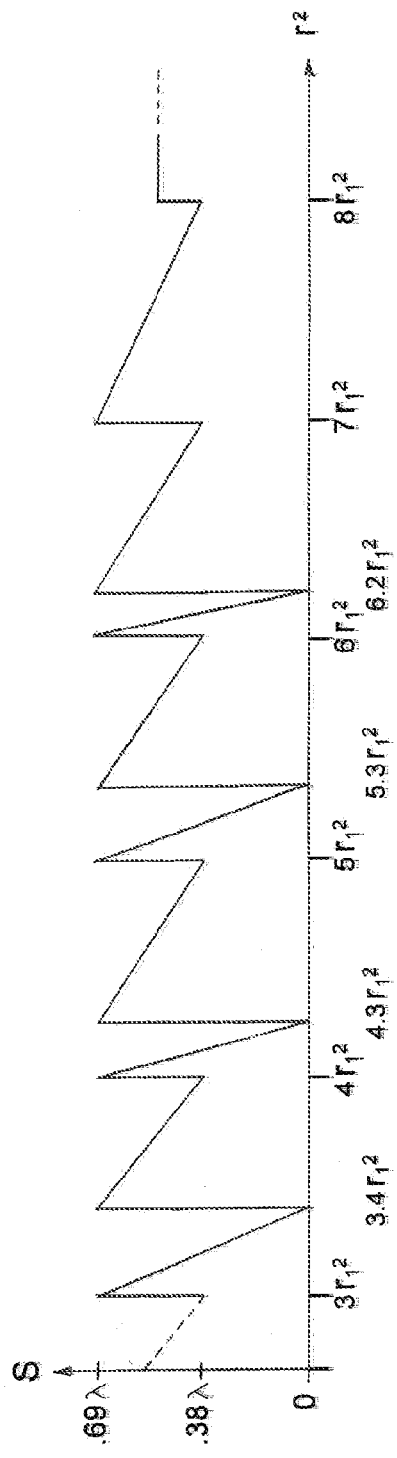
FIG. 12 illustrates the profile of zones 4 through 9 of a 14 zone lens of this invention.
Figure 13:
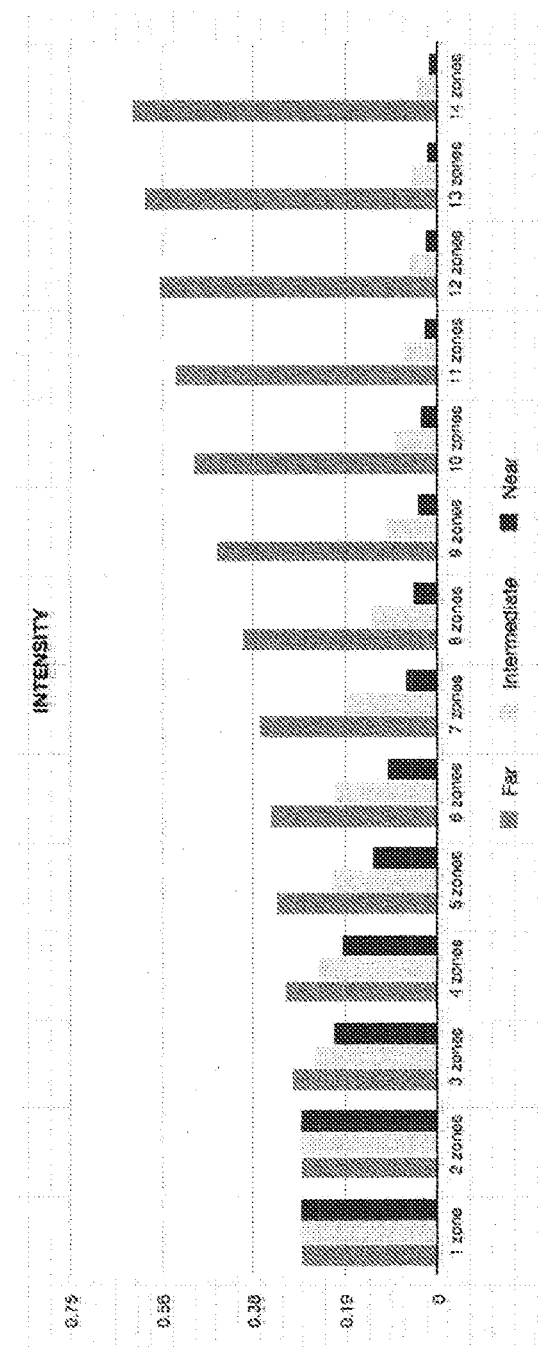
FIG. 13 illustrates the light intensity distribution of the 14 zone lens of FIG. 12.

As a second example, let us consider a 14 zone lens where the zone profiles differ from zone to zone. The parameters for this lens are shown in Table 2 and the profile (for zones 5 through 9) is illustrated in FIG. 12. The first thing that we notice looking at Table 2, is that the widths of the sub-zones change from zone to zone. So, for example, we see that in zone 1, the 1st and 2nd sub-zones are of equal area. But, in zone 3, the 1st sub-zone only has an area equal to ⅔ that of the 2nd sub-zone. And in zone 5, the 1st sub-zone only has an area equal to 3/7 of that of the 2nd sub-zone. Using formulas (12) and (13) we find that the intensities of light at orders 0th, +1, and +2, with a pupil aperture that blocks all but the first m zones are given by $\hat{\text{Im}}(0)$, $\hat{\text{Im}}(1)$, and $\hat{\text{Im}}(2)$ as shown in table 2. These light intensities are also illustrated graphically in FIG. 13.

TABLE 2

| zone (m) | a | b | c | d | q | $\hat{\text{Im}}(0)$ | $\hat{\text{Im}}(1)$ | $\hat{\text{Im}}(2)$ |
|---|---|---|---|---|---|---|---|---|
| 1 | 0.3112 | 1.0000 | 0.3112 | 0.6224 | .50 | 28% | 28% | 28% |
| 2 | 0.3112 | 1.0000 | 0.3112 | 0.6224 | .50 | 28% | 28% | 28% |
| 3 | 0.3112 | 1.0000 | 0.3112 | 0.6224 | .40 | 30% | 25% | 21% |
| 4 | 0.3112 | 1.0000 | 0.3112 | 0.6224 | .40 | 31% | 24% | 19% |
| 5 | 0.3112 | 1.0000 | 0.3112 | 0.6224 | .30 | 33% | 22% | 13% |
| 6 | 0.3112 | 1.0000 | 0.3112 | 0.6224 | .30 | 34% | 21% | 10% |
| 7 | 0.3112 | 1.0000 | 0.3112 | 0.6224 | .20 | 36% | 18% | 6% |
| 8 | 0.3112 | 1.0000 | 0.3112 | 0.6224 | .00 | 40% | 13% | 5% |
| 9 | 0.4967 | 0.4967 | 0.4967 | 0.4967 | .50 | 45% | 10% | 4% |
| 10 | 0.4967 | 0.4967 | 0.4967 | 0.4967 | .50 | 50% | 8% | 3% |
| 11 | 0.4967 | 0.4967 | 0.4967 | 0.4967 | .50 | 53% | 7% | 3% |
| 12 | 0.4967 | 0.4967 | 0.4967 | 0.4967 | .50 | 57% | 6% | 2% |
| 13 | 0.4967 | 0.4967 | 0.4967 | 0.4967 | .50 | 60% | 5% | 2% |
| 14 | 0.4967 | 0.4967 | 0.4967 | 0.4967 | .50 | 62% | 4% | 2% |

Table 2, illustrates two important features of this particular lens design. First, this lens acts as a trifocal lens when the pupil of the eye is small and acts as a single vision distance lens when the pupil is large. Second, the design of this lens rests upon the technique of "micro-modulation" wherein the relative area of the two sub-zones of each annular zones varies from zone to zone.

Heretofore, in multifocal diffractive lenses, the sub-zones within individual annular zones, have not been separately and differently altered from one annular zone to the next. This sub-zone micro-modulation allows for a much greater flexibility in lens design.

It is to be understood that there are many other useful designs that can be achieved by this method of "micro-modulation."

The invention claimed is:

1. A multifocal diffractive lens comprising a number of concentric annular zones of equal area;
   wherein at least a 1st annular zone is divided into a 1st sub-zone and a 2nd sub-zone, and a 2nd annular zone is divided into a 1st sub-zone and a 2nd sub-zone;
   wherein the 1st and 2nd sub-zones of each annular zone are each a discrete blazed step; and
   wherein said 1st sub-zone of said 1st annular zone has a different area than said 1st sub-zone of said 2nd annular zone.

2. The multifocal diffractive lens of claim 1 wherein said multifocal diffractive lens is adapted as an intraocular lens.

3. The multifocal diffractive lens of claim 2 wherein said multifocal diffractive lens is designed as a trifocal directing light into at least three different focal points.

4. The multifocal diffractive lens of claim 3 wherein said three different focal points correspond to the 0th, 1st, and 2nd diffractive orders.

5. The multifocal diffractive lens of claim 4 wherein the central zone directs at least as much light to each of the 1st and 2nd diffractive orders as it directs to the 0th diffractive order, and the peripheral most zone directs more light to the 0th order than it directs to either the 1st or 2nd diffractive orders.

6. The multifocal diffractive lens of claim 1 wherein said multifocal diffractive lens is adapted as a contact lens.

7. The multifocal diffractive lens of claim 6 wherein said multifocal diffractive lens is designed as a trifocal directing light into at least three different focal points.

8. The multifocal diffractive lens of claim 7 wherein said three different focal points correspond to the 0th, 1st, and 2nd diffractive orders.

9. The multifocal diffractive lens of claim 8 wherein the central zone directs at least as much light to each of the 1st and 2nd diffractive orders as it directs to the 0th diffractive order, and the peripheral most zone directs more light to the 0th order than it directs to either the 1st or 2nd diffractive orders.

10. A multifocal diffractive lens comprising a number of concentric annular zones of equal area;
    wherein at least a 1st and a 2nd annular zone are each divided into a 1st and a 2nd sub-zone, said 1st and 2nd sub-zones each being a discrete blazed step; and
    wherein said 1st sub-zone of said 1st annular zone has a different phase-shift than said 1st sub-zone of said 2nd annular zone.

11. The multifocal diffractive lens of claim 10 wherein said multifocal diffractive lens is adapted as an intraocular lens.

12. The multifocal diffractive lens of claim 11 wherein said multifocal diffractive lens is designed as a trifocal directing light into at least three different focal points.

13. The multifocal diffractive lens of claim 12 wherein said three different focal points correspond to the 0th, 1st, and 2nd diffractive orders.

14. The multifocal diffractive lens of claim 13 wherein the central zone directs at least as much light to each of the 1st and 2nd diffractive orders as it directs to the 0th diffractive order, and the peripheral most zone directs more light to the 0th order than it directs to either the 1st or 2nd diffractive orders.

15. The multifocal diffractive lens of claim 10 wherein said multifocal diffractive lens is adapted as a contact lens.

16. The multifocal diffractive lens of claim 15 wherein said multifocal diffractive lens is designed as a trifocal directing light into at least three different focal points.

17. The multifocal diffractive lens of claim 16 wherein said three different focal points correspond to the 0th, 1st, and 2nd diffractive orders.

18. The multifocal diffractive lens of claim 17 wherein the central zone directs at least as much light to each of the 1st and 2nd diffractive orders as it directs to the 0th diffractive order, and the peripheral most zone directs more light to the 0th order than it directs to either the 1st or 2nd diffractive orders.

19. A multifocal diffractive ophthalmic lens comprising a number of concentric annular zones of equal area;
    wherein at least one annular zone is divided into a 1st and a 2nd sub-zone, said 1st and 2nd sub-zones each being a discrete blazed step; and
    wherein said 1st sub-zone has a different area than said 2nd sub-zone.

20. The multifocal diffractive ophthalmic lens of claim 19 wherein said multifocal diffractive ophthalmic lens is designed as a trifocal directing light into at least three different focal points wherein said three different focal points correspond to the 0th, 1st, and 2nd diffractive orders.

* * * * *